US007923034B2

(12) United States Patent
Yamada et al.

(10) Patent No.: US 7,923,034 B2
(45) Date of Patent: Apr. 12, 2011

(54) PROCESS FOR PRODUCING MICROPARTICLES

(75) Inventors: Kazuhito Yamada, Ikoma (JP);
Yasumasa Sasaki, Ikoma (JP);
Fumitaka Tasaka, Ikoma (JP);
Mitsuaki Kuwano, Ikoma (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 201 days.

(21) Appl. No.: 10/559,173

(22) PCT Filed: Jun. 3, 2004

(86) PCT No.: PCT/JP2004/008047
§ 371 (c)(1),
(2), (4) Date: Dec. 1, 2005

(87) PCT Pub. No.: WO2004/108115
PCT Pub. Date: Dec. 16, 2004

(65) Prior Publication Data
US 2006/0134223 A1 Jun. 22, 2006

(30) Foreign Application Priority Data
Jun. 3, 2003 (JP) .................................. 2003-158085

(51) Int. Cl.
*A61K 9/50* (2006.01)
(52) U.S. Cl. ........................................ 424/490; 264/4.1
(58) Field of Classification Search .................. 514/317, 514/217, 469, 649, 378, 618, 225.8; 424/722, 424/490; 264/4.1
See application file for complete search history.

(56) References Cited

U.S. PATENT DOCUMENTS

| | | | | |
|---|---|---|---|---|
| 4,542,025 | A * | 9/1985 | Tice et al. ..................... | 424/497 |
| 6,214,387 | B1 | 4/2001 | Berde et al. | |
| 2002/0009493 | A1 | 1/2002 | Schwendeman et al. | |

FOREIGN PATENT DOCUMENTS

| | | |
|---|---|---|
| EP | 0 269 921 A1 | 6/1988 |
| EP | 0 377 477 A1 | 7/1990 |
| EP | 0 461 630 A2 | 12/1991 |
| JP | 60-67417 A | 4/1985 |
| JP | 4-46115 A | 2/1992 |
| JP | 5-58882 A | 3/1993 |
| JP | 6-87758 A | 3/1994 |
| JP | 9-505308 A | 5/1997 |
| JP | 10-7583 A | 1/1998 |
| JP | 10-273447 A | 10/1998 |
| JP | 2002-138036 A | 5/2002 |
| WO | WO 95/13799 A1 | 5/1995 |
| WO | WO 99/24061 A1 | 5/1999 |

OTHER PUBLICATIONS

T.R. Rice et al, "Preparation of Injectable Controlled-Release Microcapsules by a Solvent-Evaporation Process", *Journal of Controlled Release*, 2, pp. 343-352 (1985).
Chaw C.S. et al., "Water-soluble betamethasone-loaded poly(lactide-co-glycolide) hollow microparticles as a sustained release dosage form," *Journal of Microencapsulation*, Taylor and Francis, Basingstoke, GB, vol. 20, No. 3, May 1, 2003, pp. 349 to 359.
Lamprecht A. et al., "Biodegradable microparticles as a two-drug controlled release formulation: a potential treatment of inflammatory bowel disease," *Journal of Controlled Release*, Elsevier, Amsterdam, NL, vol. 69, No. 3, Dec. 3, 2000, pp. 445 to 454.
Supplementary European Search Report dated Mar. 15, 2010 for European application 04 73 5976.

* cited by examiner

*Primary Examiner* — Sreeni Padmanabhan
*Assistant Examiner* — Sahar Javanmard
(74) *Attorney, Agent, or Firm* — Holtz, Holtz, Goodman & Chick, P.C.

(57) ABSTRACT

An object of the present invention is to provide a solvent which is able to produce microparticles where content of the drug is still high and no initial burst takes place even when a drug having a low solubility in a halogenated hydrocarbon solvent is used. The present invention provides a process for production by a solvent-evaporation microencapsulation method, of microparticles which are composed of biodegradable polymer and contain a drug having a low solubility in a halogenated hydrocarbon, which is characterized in that the drug and the biodegradable polymer are dissolved in a mixed solvent comprising a first solvent: halogenated hydrocarbon, and a second solvent: a water-immiscible organic solvent in which solubility of the above-mentioned drug is 0.3% (w/v) or more.

12 Claims, 1 Drawing Sheet

PROCESS FOR PRODUCING MICROPARTICLES

This application is the United States national phase application of International Application PCT/JP2004/008047 filed Jun. 3, 2004.

TECHNICAL FIELD

The present invention relates to a process for producing microparticles.

BACKGROUND ART

With regard to pharmaceutical preparations useful for sustained release of drugs, many studies have been conducted for microparticles such as microspheres and nanospheres using biodegradable polymers. Various methods have been known as a process for producing such microparticles and one of them is a solvent-evaporation microencapsulation method. As shown in Journal of Controlled Release, 2, 343-352, 1985, the solvent-evaporation microencapsulation method is a method for producing microparticles where a drug and a polymer which is a material for microparticles are dissolved in a volatile organic solvent and added to an aqueous phase to prepare an o/w type emulsion and the organic solvent is evaporated whereupon microparticles are produced. As to the solvent to be used in a solvent-evaporation microencapsulation method, it is preferred to be volatile and immiscible with water and halogenated hydrocarbons such as dichloromethane and chloroform have been widely used.

A process for producing microparticles where no halogenated hydrocarbon solvent is used has been known as well. In JP-T-9-505308, a process for producing microparticles using a mixed solvent comprising at least two among ester, alcohol and ketone is disclosed and, as examples of preferred solvents, ethyl acetate, benzyl alcohol, methyl ethyl ketone, etc. are listed. In the Examples therein, an example for producing microparticles using a mixed solvent of ethyl acetate and benzyl alcohol is mentioned.

However, halogenated hydrocarbon is an excellent solvent in view of volatility, property of formation of emulsion and solubility for biopolymers and, therefore, it is desirable to use a solvent of a halogenated hydrocarbon type for the production of microparticles.

Incidentally, when solubility of a drug in a halogenated hydrocarbon solvent is low, it is to be produced by dispersing the drug in the halogenated hydrocarbon solvent, but, in such a process, although the drug content incorporated in the microparticles becomes high, the drug is present concentratedly around the outer side of the microparticles whereby there is a problem of an excessive release in the initial stage of the release (initial burst).

Under such circumstances, in order to increase the solubility of a drug in an oily phase, it has been known to add a water-miscible solvent such as methanol or acetonitrile to a halogenated hydrocarbon (refer to JP-A-4-46115). However, in such a process, although a drug is able to be dissolved in the solvent, it is still impossible to give sufficient drug content and an initial burst is also noted. The causes therefor are that, since a solvent such as methanol or acetonitrile is miscible with water, leakage of the drug to the outer aqueous phase is larger during the production step, that the drug is not uniformly dispersed in the resulting microparticles and that the resulting microparticles are porous.

DISCLOSURE OF THE INVENTION

As such, when a drug having a low solubility in halogenated hydrocarbon solvent is used in the solvent-evaporation microencapsulation method where halogenated hydrocarbon is used as a solvent, amount of the drug contained therein is low and the initial burst takes place as well. Thus, there has been a demand for a solvent which is able to produce microparticles where content of the drug is still high and no initial burst takes place even when a drug having a low solubility in a halogenated hydrocarbon solvent is used.

The present inventors have conducted an intensive study for a solvent used in a process for production of microparticles which is composed of biodegradable polymer and contains a drug having a low solubility in a halogenated hydrocarbon by a solvent-evaporation microencapsulation method and, as a result, they have found that, when a mixed solvent comprising the first solvent: halogenated hydrocarbon, and
the second solvent: water-immiscible organic solvent in which solubility of the aforementioned drug is 0.3% (w/v) or higher is used as a solvent for dissolving the drug and the biodegradable polymer, it is possible to produce microparticles where amount of the drug contained therein is large, no initial burst takes place and the drug is able to release in a zero-order manner for a long period.

The present invention is a process for production of microparticles which are composed of biodegradable polymer and contain a drug having a low solubility in a halogenated hydrocarbon by a solvent-evaporation microencapsulation method, characterized in that the drug and the biodegradable polymer are dissolved in a mixed solvent comprising a halogenated hydrocarbon (the first solvent) and a water-immiscible organic solvent in which the aforementioned drug is soluble to an extent of 0.3% (w/v) or more (the second solvent).

The present invention is a process for producing microparticles which is applied to a drug having a low solubility in a halogenated hydrocarbon and, to be more specific, solubility of the drug in the halogenated hydrocarbon is less than 0.1% (w/v). Examples of such a drug are steroidal agents such as betamethasone, dexamethasone, prednisolone and derivatives thereof.

The first solvent in the present invention is a halogenated hydrocarbon or alkyl halide having 1 to 4 carbon(s) and, to be more specific, it is dichloromethane, chloroform, carbon tetrachloride, dichloroethane, 2,2,2-trichloroethane or the like. Preferably, dichloromethane and chloroform are used.

The present invention is characterized by mixing a halogenated hydrocarbon (the first solvent) with the water-immiscible organic solvent (the second solvent) where solubility of a drug therein is 0.3% (w/v) or higher. As a result, a drug having a low solubility in a halogenated hydrocarbon is able to be dissolved in an oily phase. Solubility of a drug in the second solvent is preferably 0.3 to 50% (w/v) and, particularly preferably, 0.5 to 30% (w/v).

Further, since the second solvent is a water-immiscible organic solvent unlike acetonitrile, methanol, etc., it is possible that leakage of the drug into an aqueous phase is suppressed and that the drug is able to be uniformly dispersed in microparticles. To be more specific, solubility of the second solvent in water is preferably 1.0 to 30% (v/v).

With regard to the second solvent, an appropriate water-immiscible organic solvent may be selected depending upon the drug which is an object. For example, in the case of steroid having low solubility in a halogenated hydrocarbon such as betamethasone, the second solvents are exemplified by phenylalkyl alcohol such as benzyl alcohol and phenylethyl alcohol; ketone such as methyl ethyl ketone, methyl butyl ketone and methyl isopropyl ketone; aniline; and 1-butanol. In the case of betamethasone, benzyl alcohol is particularly preferred.

Although there is no particular limitation for a mixing ratio of the first solvent to the second solvent and that may be appropriately changed depending upon the type of a drug, effective therapeutic concentration of a drug, a releasing period, etc., it is preferably 1:20 to 20:1 and, particularly preferably, 1:1 to 1:10.

With regard to the biodegradable polymer in the present invention, its examples are poly(lactic acid), (lactic acid)-(glycolic acid) copolymer (hereinafter, abbreviated as PLGA), (lactic acid)-caprolactone copolymer, polyanhydride, polyorthoester, poly(-ε-caprolactone), polyacryl cyanoacrylate, polyhydroxy alkanoate, polyphosphoester, polyamino acid and poly(α-hydroxylic acid). Preferably, poly(lactic acid) and PLGA are used. Ratio of lactic acid to glycolic acid in PLGA is preferable 10:1 to 1:10.

There is no particular limitation for weight-average molecular weight of the biodegradable polymers as such and that may be appropriately selected depending upon the type of a drug to be contained in the microparticles, effective therapeutic concentration of a drug, releasing period of a drug, etc. In the case of poly(lactic acid) and PLGA, it is preferred to be 5,000 to 70,000.

The microparticles produced by the present invention are microparticles containing a drug and a biodegradable polymer and examples thereof are microparticles in a capsule form where one drug core is contained in one particle, multinuclear capsule shaped microparticles where a number of drug cores are contained in one particle and microparticles where the drug is dissolved or dispersed in the biodegradable polymer. Particle size of the microparticle is preferably 500 nm to 150 μm.

The production process according to the present invention will be illustrated in detail as hereunder.

A drug and a biodegradable polymer are dissolved in a mixed solvent of the first and the second solvents to form an oily phase. Concentration of the drug in this solvent (i.e., an oily phase) is, for example, 0.1 to 50% (w/v) and, preferably, 0.3 to 10% (w/v). Concentration of the biodegradable polymer in the solution is, for example, 0.1 to 80% (w/v) and, preferably, 2 to 50% (w/v). Although ratio by weight of the drug to the polymer varies depending upon the type of the drug, necessary content of the drug in the microparticles, etc., it is preferably 1:20 to 1:1.

The aforementioned oily phase is added to an outer aqueous phase at a constant rate and dispersed/emulsified using a homo-mixer or the like to prepare an o/w type emulsion. Amount of the outer aqueous phase used is usually 10- to 400-fold by volume and, preferably, 50- to 200-fold of the oily phase. An emulsifier can be added to the outer aqueous phase. Examples of the emulsifier are polysorbate 80, polyvinyl alcohol, polyvinylpyrrolidone, carboxymethyl cellulose and lecithin and polyvinyl alcohol is particularly preferred. Concentration of the emulsifier in the outer aqueous phase is, for example, 0.01 to 20% (w/v) and, particularly preferably, 0.02 to 2% (w/v).

Removal of the oily phase may be carried out by a conventionally used method. For example, there is a method where the resulting o/w type emulsion is allowed to stand with stirring using a propeller-type stirrer or is heated, or nitrogen gas is blown to the emulsion. It is also possible that pressure is gradually reduced to remove the solvent or degree of vacuum is adjusted using a rotary evaporator or the like to remove the solvent. The microparticles produced as such is recovered by centrifugal separation or filtration, washed with pure water and freeze-dried to give an aimed product.

The microparticles produced by the process of the present invention are able to be made into pharmaceutical preparations of various dosage forms. Examples of the dosage form are injection preparations, implant preparations, orally preparations, eye drops and nasally administering preparations and injection preparations are particularly preferred. The injection preparation can be prepared by a widely used technique for preparing an injection preparation. For example, microparticles and widely used additives are added to distilled water for injection whereupon an injection preparation is prepared. Examples of the additives are an adjusting agent for osmotic pressure such as sodium chloride, a buffer such as sodium phosphate, a surfactant such as polysorbate 80 and a viscous agent such as methyl cellulose.

According to the present invention, the following advantages are achieved. Thus, as will be apparent from the result of "Result of measurement of drug content" and "In vitro releasing test" which will be mentioned later, microparticles which is produced by such a manner that a drug having a low solubility in halogenated hydrocarbon is dissolved in a mixed solvent comprising a halogenated hydrocarbon and a water-immiscible organic solvent where solubility of a drug therein is 0.3% or more has a high drug content in the microparticles, are free from initial burst and are able to release the drug in a zero-order manner for a long period.

BEST MODE FOR CARRYING OUT THE INVENTION

Figure 1:
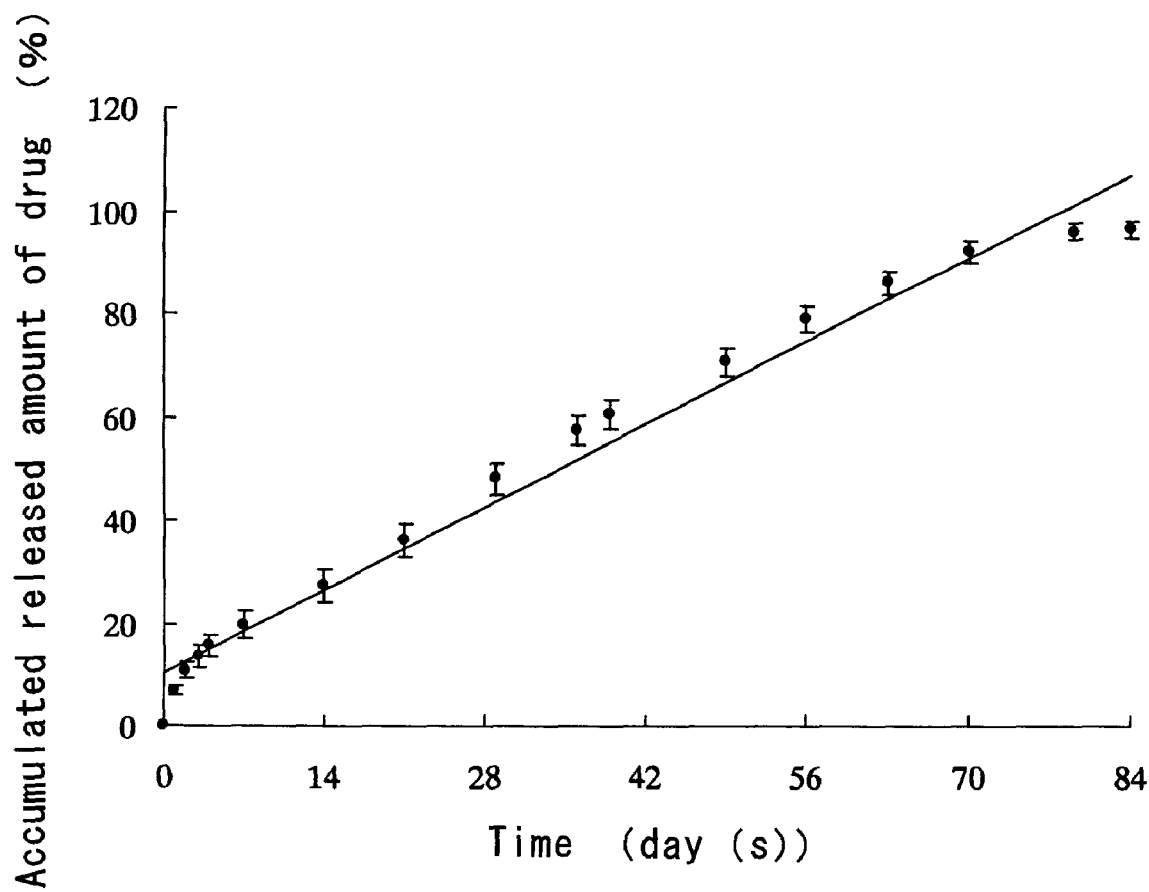
FIG. 1 is a graph which shows the changes in drug release with a lapse of time from the microparticles produced in Production Example 4.

A production process of the present invention will now be illustrated in detail by way of the following Examples although the present invention is not limited thereto.

Production Example 1

Betamethasone (0.05 g) and (lactic acid)-(glycolic acid) copolymer (0.25 g) having a weight-average molecular weight of 20,000 were dissolved in a mixture of dichloromethane (1 mL) and benzyl alcohol (3 mL). The resulting solution was dropped into 400 mL of a 2% aqueous solution of polyvinyl alcohol and the whole was mixed for about 10 minutes using a small homogenizer (Polytron; manufactured by Kinematica, Switzerland) to form an o/w type emulsion. Next, microparticles were produced by removal of dichloromethane and benzyl alcohol by stirring the o/w emulsion and then collected with a centrifugal separator. They were dispersed in distilled water again and centrifuged and then drug, dispersing agent, etc. which were liberated therefrom were removed by washing. The collected microparticles were freeze-dried so that the solvents and water were completely removed to give powder. In the microparticles produced by the above-mentioned process, particle size (median diameter) was 14 μm, the drug content was 11%, the recovery rate of microparticles was 71% and the drug encapsulation rate was 50%.

Production Example 2

The same operation was carried out as in Production Example 1 except that betamethasone (0.05 g) and (lactic acid)-(glycolic acid) copolymer (0.25 g) having a weight-average molecular weight of 20,000 were dissolved in a mixture of dichloromethane (1 mL) and phenylethyl alcohol (3 mL). In the resulting microparticles, particle size (median diameter) was 16 μm, the drug content was 8%, the recovery rate of microparticles was 74% and the drug encapsulation rate was 37%.

Production Example 3

The same operation was carried out as in Production Example 1 except that betamethasone (0.025 g) and poly (lactic acid) (0.25 g) having a weight-average molecular weight of 20,000 were dissolved in a mixture of dichloromethane (1 mL) and benzyl alcohol (1.5 mL) and that the resulting solution was dropped into 200 mL of a 2% aqueous solution of polyvinyl alcohol. In the resulting microparticles, the drug content was 1.33%.

Production Example 4

The same operation was carried out as in Production Example 3 except that betamethasone (0.05 g) and poly(lactic acid) (0.25 g) having a weight-average molecular weight of 20,000 were dissolved in a mixture of dichloromethane (1 mL) and benzyl alcohol (3 mL). In the resulting microparticles, the drug content was 7.76%.

Comparative Production Example 1

The same operation was carried out as in Production Example 1 except that betamethasone (0.025 g) and poly (lactic acid) (0.25 g) having a weight-average molecular weight of 20,000 were dissolved in dichloromethane (40 mL) and that the resulting dispersion was dropped into 200 mL of a 2% aqueous solution of polyvinyl alcohol to give microparticles.

Comparative Production Example 2

The same operation was carried out as in Production Example 1 except that betamethasone (0.05 g) and (lactic acid)-(glycolic acid) copolymer (0.25 g) having a weight-average molecular weight of 20,000 were dissolved in a mixture of ethyl acetate (1 mL) and benzyl alcohol (3 mL). In the resulting microparticles, particle size (median diameter) was 15 μm, the drug content was 14%, the recovery rate of microparticles was 66% and the drug encapsulation rate was 54%.

Comparative Production Example 3

The same operation was carried out as in Production Example 1 except that betamethasone (0.05 g) and (lactic acid)-(glycolic acid) copolymer (0.25 g) having a weight-average molecular weight of 20,000 were dissolved in a mixture of ethyl formate (1 mL) and benzyl alcohol (3 mL). In the resulting microparticles, particle size (median diameter) was 14 μm, the drug content was 13%, the recovery rate of microparticles was 57% and the drug encapsulation rate was 43%.

Test for Measurement of Drug Content

In order to investigate the influence of a solvent used for the production of microparticles on drug content of the microparticles, drug contents of the microparticles produced in Production Example 3 and Comparative Production Example 1 were measured by the following method.

<Method for Measurement of Drug Content>

Betamethasone-containing microparticles (2 mg) were dissolved in acetonitrile (1 mL) and a 50 mM potassium phosphate/methanol solution was added thereto to make 10 mL. The resulting mixture was filtered using a filter (0.2 μm) to recover a filtrate. The obtained filtrate was quantified using a high-performance liquid chromatography and the content of betamethasone in the microparticles was calculated.

<Result>

The result is shown in Table 1. As will be apparent from Table 1, it is shown that, in the microparticles (Comparative Production Example 1) produced by a conventional method where drug and polymer are dissolved only in a halogenated hydrocarbon in the process for producing betamethasone-containing microparticles, drug content is low while, in the microparticles (Production Example 3) produced by the process of the present invention, drug content is significantly high.

TABLE 1

Drug Content (%)

| | Solvent(s) | Drug Content (%) |
|---|---|---|
| Production Example 3 | Dichloromethane/Benzyl Alcohol | 1.33 |
| Comparative Production Example 1 | Dichloromethane | 0.04 |

The value of drug content in Production Example 3 is a mean value of five measured values and that of Comparative Production Example 1 is a mean value of three measured values.

In Vitro Releasing Test (1)

In order to study the influence of the solvents used for the production of microparticles on the initial drug-releasing property, initial drug-releasing rates of microparticles produced by Production Examples 1 to 2 and Comparative Production Examples 2 to 3 were measured.

<Method for Measurement of Initial Releasing Rate>

Microparticles (4 mg) were shaken in 0.1M phosphate buffer (pH 7.4) and, after one day, betamethasone was quantified in 0.1M phosphate buffer (pH 7.4) thereby the initial drug-releasing rate of the drug in vitro was measured.

<Result>

The result is shown in Table 2. It is shown from Table 2 that the initial burst of the drug is lower in the microparticles produced by the process of the present invention (Production Examples 1 and 2) than in the microparticles produced using a non-halogenated solvent and phenylalkyl alcohol (Comparative Production Examples 2 and 3).

TABLE 2

Initial Drug Releasing Rate (%)

| | Solvents | Initial Releasing Rate (%) |
|---|---|---|
| Production Example 1 | Dichloromethane/Benzyl Alcohol | 11.43 |
| Production. Example 2 | Dichloromethane/Phenylethyl Alcohol | 9.05 |
| Comp. Prodn. Ex. 2 | Ethyl Acetate/Benzyl Alcohol | 24.06 |
| Comp. Prodn. Ex. 3 | Ethyl Formate/Benzyl Alcohol | 19.72 |

Values of initial releasing rates of Production Example 1 and Comparative Production Examples 2 and 3 are mean values of three measured values and the value of initial releasing rate of Production Example 2 is a mean value of one measured value.

In Vitro Releasing Test (2)

In order to study the drug-releasing characteristic of the microparticles of the present invention for a long period of time, the released amount of the drug from the microparticles produced by Production Example 4 was measured with a lapse of time. Method for the measurement was the same as that in the above-mentioned in vitro drug-releasing test (1) and measurement was conducted for three months.

<Result>

The result is shown in FIG. 1. It is shown from FIG. 1 that the microparticles produced by the process of the present invention are free from initial burst of the drug and are able to release the drug in a zero-order manner for three months.

INDUSTRIAL APPLICABILITY

In accordance with the present invention, it is possible to produce microparticles where drug content is high and initial burst does not take place even when solubility of the drug in a halogenated hydrocarbon is low.

The invention claimed is:

1. A process for production, by a solvent-evaporation microencapsulation method, of microparticles which are composed of a biodegradable polymer and contain a steroid agent, wherein the steroid agent and the biodegradable polymer are dissolved in a mixed solvent comprising dichloromethane and a phenylalkyl alcohol, wherein a mixing ratio of the dichloromethane to the phenylalkyl alcohol is 1:1 to 1:10, a particle size of the microparticles is 500 nm to 150 μm and an initial burst of the steroid agent in the microparticles is lower than in microparticles produced using a non-halogenated solvent and phenylalkyl alcohol.

2. The process for production according to claim 1, wherein the steroid agent is betamethasone, dexamethasone or prednisolone.

3. The process for production according to claim 1, wherein the biodegradable polymer is poly(lactic acid) or (lactic acid)-(glycolic acid) copolymer.

4. A process for production of microparticles in which a steroid agent and a biodegradable polymer are dissolved in a mixed solvent comprising dichloromethane and a phenylalkyl alcohol to form an oily phase, the oily phase is mixed with an aqueous phase to form an o/w type emulsion and then said mixed solvent is removed to produce the microparticles, wherein a mixing ratio of the dichloromethane and the phenylalkyl alcohol is 1:1 to 1:10, a particle size of the microparticles is 500 nm to 150 μm, and an initial burst of the steroid agent in the microparticles is lower than in microparticles produced using a non-halogenated solvent and phenylalkyl alcohol.

5. The process for production according to claim 1, wherein the steroid agent is betamethasone; the biodegradable polymer is poly(lactic acid) or (lactic acid)-(glycolic acid) copolymer; and the phenylalkyl alcohol is benzyl alcohol.

6. The process for production according to claim 4, wherein the steroid agent is betamethansone; the biodegradable polymer is poly(lactic acid) or (lactic acid)-(glycolic acid) copolymer; and the phenylalkyl alcohol is benzyl alcohol.

7. An injection preparation comprising the microparticles produced by the process according to claim 1.

8. An injection preparation comprising the microparticles produced by the process according to claim 2.

9. An injection preparation comprising the microparticles produced by the process according to claim 3.

10. An injection preparation comprising the microparticles produced by the process according to claim 4.

11. An injection preparation comprising the microparticles produced by the process according to claim 5.

12. An injection preparation comprising the microparticles produced by the process according to claim 6.

* * * * *